(12) United States Patent
O'Connor et al.

(10) Patent No.: US 10,927,390 B2
(45) Date of Patent: Feb. 23, 2021

(54) METHOD FOR PRODUCING LACTIC ACID BY BACTERIAL FERMENTATION

(71) Applicant: Glanbia Ireland Designated Activity Company, Co. Kilkenny (IE)

(72) Inventors: Kevin O'Connor, Co. Dublin (IE); Shane Kenny, Co. Wicklow (IE); Maciej Guzik, Dublin (IE); Bill Morrissey, Co. Tipperary (IE); Colm O'Brien, Co. Limerick (IE)

(73) Assignee: GLANBIA IRELAND DESIGNATED ACTIVITY COMPANY, Ballyraggat (IE)

( * ) Notice: Subject to any disclaimer, the term of this patent is extended or adjusted under 35 U.S.C. 154(b) by 0 days.

(21) Appl. No.: 15/772,046

(22) PCT Filed: Nov. 1, 2016

(86) PCT No.: PCT/IE2016/000020
§ 371 (c)(1),
(2) Date: Apr. 27, 2018

(87) PCT Pub. No.: WO2017/072748
PCT Pub. Date: May 4, 2017

(65) Prior Publication Data
US 2018/0312885 A1    Nov. 1, 2018

(30) Foreign Application Priority Data
Oct. 30, 2015 (EP) .................................... 15192439

(51) Int. Cl.
*C12P 7/56* (2006.01)
*C12N 1/36* (2006.01)
*C12R 1/07* (2006.01)

(52) U.S. Cl.
CPC ................. *C12P 7/56* (2013.01); *C12N 1/36* (2013.01); *C12R 1/07* (2013.01); *C12N 2500/84* (2013.01)

(58) Field of Classification Search
None
See application file for complete search history.

(56) References Cited

U.S. PATENT DOCUMENTS

| | | | |
|---|---|---|---|
| 4,467,034 | A | 8/1984 | Voelskow et al. |
| 5,322,781 | A | 6/1994 | Veringa |
| 5,416,020 | A | 5/1995 | Severson et al. |
| 5,801,025 | A | 9/1998 | Ohara et al. |
| 2011/0306083 | A1 | 12/2011 | Mucha |
| 2019/0166865 | A1 | 6/2019 | Morrissey et al. |

FOREIGN PATENT DOCUMENTS

| | | |
|---|---|---|
| EP | 0770684 A | 5/1997 |
| WO | 99/04903 A1 | 2/1999 |
| WO | 01/92555 A1 | 12/2001 |
| WO | 2010103548 A2 | 9/2010 |

OTHER PUBLICATIONS

Payot, T; et al; "Lactic acid production by *Bacillus coagulans*—Kinetic studies and optimization of culture medium for batch and continuous fermentations" Enzyme and Microbial Technology, 24, 191-199, 1999 (Year: 1999).*

International Search Report and Written Opinion for Int'l Application No. PCT/IE2016/000020, titled: A Method for Producing Lactic Acid by Bacterial Fermentation, dated Jan. 20, 2017.

Blascovich, "L-Latic acid production by bacteria", URL: http://www.ucd.ie/science/international_students/poster/liz_blascovich.pdf, p. 1 (2013).

Blascovich, "UCD Science Study Abroad Research Projects", University College Dublin, URL: http://www.ucd.ie/science/international_students/ (2014).

Abdel-Rahman et al., "Recent advances in lactic acid production by microbial fermentation processes", Biotechnology Advances, vol. 31, No. 6, pp. 877-902 (2013).

Michelson et al., "L(+)-Lactic acid producer *Bacillus coagulans* SIM-7 DSM 14043 and its comparison with *Lactobacillus delbrueckii* ssp. lactis DSM 20073" Enzyme and Microbial Technology, Stoneham, MA, US, vol. 39, No. 4, pp. 861-867 (2006).

Hu et al., "High-titer lactic acid production from NaOH-pretreated corn stover by *Bacillus coagulans* LA204 using fed-batch simultaneous saccharification and fermentation under non-sterile condition," Bioresource Technology, vol. 182, Feb. 11, 2015, pp. 251-257.

Juturu et al., "Production of high concentration of L-lactic acid from oil palm empty fruit bunch by thermophilic *Bacillus coagulans* JI12," Biotechnology and Applied Biochemistry, 2018 (published online Jul. 11, 2017), pp. 145-149.

Ou et al., "L(+)-Lactic acid production from non-food carbohydrates by thermotolerant *Bacillus coagulans*," J. Ind. Microbiol. Biotechnol., vol. 38, 2011 (published online Aug. 9, 2010), pp. 599-605.

Ouyang et al., "Open fermentative production of L-lactic acid by *Bacillus* sp. strain NL01 using lignocellulosic hydrolyzates as low-cost raw material," Bioresource Technology, vol. 135, Oct. 5, 2012, pp. 475-480.

Pleissner et al., "Separation of lactic acid and recovery of salt-ions from fermentation broth," J. Chem. Technol. Biotechnol., Society of Chemical Industry, Research Article, Wiley Online Library, vol. 92, Jun. 22, 2016, pp. 504-511.

(Continued)

*Primary Examiner* — David W Berke-Schlessel
(74) *Attorney, Agent, or Firm* — Hamilton, Brook, Smith & Reynolds, P.C.

(57) ABSTRACT

A method for producing lactic acid comprises the steps of culturing in a culture medium comprising concentrated whey permeate or delactosed whey permeate as a substrate a bioconversion competent *Bacillus* bacterial strain capable of converting delactosed whey permeate into lactic acid for a period of time sufficient to allow the bacteria convert at least some of the lactose present in DLP or concentrated whey permeate into lactic acid, and then recovering the lactic acid from the culture medium.

13 Claims, No Drawings

(56) References Cited

OTHER PUBLICATIONS

Rosenberg et al., "High temperature lactic acid production by *Bacillus coagulans* immobilized in LentiKats," Biotechnology Letters, vol. 27, 2005, pp. 1943-1947.
Sun et al., "Diammonium phosphate stimulates transcription of L-lactate dehydrogenase leading to increased L-lactate production in the thermotolerant *Bacillus coagulans* strain," Appl. Microbiol. Biotechnol., vol. 100, Feb. 17, 2016, pp. 6653-6660.
Ye et al., "Highly efficient production of L-lactic acid from xylose by newly isolated *Bacillus coagulans* C106," Bioresource technology, vol. 132, Jan. 16, 2013, pp. 38-44.
Zhou et al., "Efficient production of L-lactic acid by newly isolated thermophilic *Bacillus coagulans* WCP10-4 with high glucose tolerance," Appl. Microbiol. Biotechnol., vol. 97, Jan. 25, 2013, pp. 4309-4314.
PubChem [Internet]. Bethesda (MD): National Library of Medicine (US), National Center for Biotechnology Information; 2004-. PubChem Compound Summary for CID 612, Lactic acid; [cited Aug. 12, 2020]. Available from: https:/pubchem.ncbi.nlm.nih.gov/compound/Lactic-acid.
Office Action for U.S. Appl. No. 16/324,117, titled: "A Method of Producing Lactic Acid", dated Aug. 17, 2020.
International Preliminary Report on Patentability for International Application No. PCT/EP2017/070120, "A Method of Producing Lactic Acid" dated Feb. 12, 2019.
International Search Report and the Written Opinion for International Application No. PCT/EP2017/070120, "A Method Of Producing Lactic Acid" dated Nov. 22, 2017.

\* cited by examiner

METHOD FOR PRODUCING LACTIC ACID BY BACTERIAL FERMENTATION

This application is the U.S. National Stage of International Application No. PCT/IE2016/000020, filed on Nov. 1, 2016, which designates the U.S., published in English, and claims priority under 35 U.S.C. § 119 or 365(c) to European Application No. 15192439.6, filed on Oct. 30, 2015. The entire teachings of the above applications are incorporated herein by reference.

TECHNICAL FIELD

The invention relates to a method of producing lactic acid. In particular, the invention relates to a method for producing lactic acid by means of bacterial fermentation of a substrate.

BACKGROUND TO THE INVENTION

Delactosed whey permeate (DLP) is a by-product of whey processing. DLP contains high concentrations of sodium chloride, phosphates, and 200-400 g of lactose per litre of DLP. The lactic acid producing bacteria cannot grow on DLP in batch fermentation, as DLP inhibits the growth of bacteria even at low concentrations. It is an object of the invention to overcome at least one of the above-referenced problems.

STATEMENTS OF INVENTION

The Applicant has discovered that *Bacillus* bacteria, in particular *Bacillus coagulans*, are capable of growing on substrates such as delactosed whey permeate (DLP) and converting DLP into lactic acid in an efficient and industrially-relevant manner. This is surprising as DLP contains high amounts of salt, sugars, and minerals, which present osmotic and chloride challenges, which are considered to be highly detrimental to bacterial growth. Moreover, *lactobacillus* bacteria are normally associated with bioconversion of lactose to lactic acid, not *bacillus* species. The applicant provides data showing that a wild-type *Bacillus coagulans* strain (MG-2) isolated from soil, and two adapted *Bacillus coagulans* strains produced from a reference deposited *Bacillus coagulans* strain, are capable of growing on culture media containing high amounts of DLP (30-50% weight per volume (w/v)) and converting delactosed whey permeate into lactic acid in an efficient and industrially-relevant manner in batch and fed-batch fermenters.

Accordingly, the invention provides a method for producing lactic acid comprising steps of:
culturing in a culture medium comprising whey permeate or delactosed whey permeate as a substrate a bioconversion competent bacterial strain capable of converting delactosed whey permeate into lactic acid; and
optionally recovering the lactic acid from the culture medium.

In one embodiment, the substrate is delactosed whey permeate (DLP). In one embodiment, the DLP contains at least 240 g lactose per litre DLP. In one embodiment, the DLP contains at least 15,000 ppm chloride.

In one embodiment, the substrate is concentrated whey permeate (CWP). In one embodiment, the CWP contains at least 200 g lactose per litre CWP. In one embodiment, the CWP contains at least 5,000 ppm chloride.

In one embodiment, the bioconversion competent bacterial strain is a *Bacillus* strain.

In one embodiment, the bioconversion competent *bacillus* strain is a strain of *Bacillus coagulans*.

In one embodiment, the bioconversion competent *Bacillus* strain is capable of growing on a test culture medium containing at least 10% delactosed whey permeate (v/v).

In one embodiment, the bioconversion competent *Bacillus* strain is capable of growing on a test culture medium containing at least 20% delactosed whey permeate (v/v).

In one embodiment, the bioconversion competent *Bacillus* strain is capable of growing on a test culture medium containing at least 30% delactosed whey permeate (v/v).

In one embodiment, the bioconversion competent *Bacillus* strain is capable of growing on a test culture medium containing at least 40% delactosed whey permeate (v/v).

In one embodiment, the bioconversion competent *Bacillus* strain is capable of growing on a test culture medium containing at least 50% delactosed whey permeate (v/v).

In one embodiment, the bioconversion competent *Bacillus* strain is a wild-type *Bacillus* strain (such as MG-2).

In one embodiment, the bioconversion competent *bacillus* strain is an adapted *Bacillus* strain that is adapted to grow in delactosed whey permeate (such as UCD1 and UCD2).

In one embodiment, the adapted *bacillus* strain is a derivative of a wild-type *Bacillus* strain.

In one embodiment, the bioconversion competent *Bacillus* strain is capable of growing on a test culture medium supplemented with DLP and converting it into lactic acid at least at 100 g lactic acid per litre of DLP with a yield of greater than 85%. Typically, the process includes a step of recovering lactic acid at a yield of at least 100 g lactic acid per litre of DLP.

In one embodiment, the bioconversion competent *Bacillus* strain is capable of growing on a test culture medium supplemented with 10% delactosed whey permeate (v/v) and producing lactic acid typically a yield of at least 90% (w/w). Typically, the process includes a step of recovering lactic acid at a yield of at least 95% (v/v).

In one embodiment, the bioconversion competent *Bacillus* strain is capable of growing on a test culture medium supplemented with 20% delactosed whey permeate (v/v) and producing lactic acid typically with a yield of at least 90% (w/w). Typically, the process includes a step of recovering lactic acid at a yield of at least 95% (v/v).

In one embodiment, the bioconversion competent *Bacillus* strain is capable of growing on a test culture medium supplemented with 30% delactosed whey permeate (v/v) and producing lactic acid typically with a yield of at least 90% (w/w). Typically, the process includes a step of recovering lactic acid at a yield of at least 95% (v/v).

In one embodiment, the bioconversion competent *Bacillus* strain is capable of growing on a test culture medium supplemented with 40% delactosed whey permeate (v/v) and producing lactic acid typically with a yield of at least 90% (w/w). Typically, the process includes a step of recovering lactic acid at a yield of at least 95% (v/v).

In one embodiment, the bioconversion competent *Bacillus* strain is capable of growing on a test culture medium supplemented with 50% delactosed whey permeate (v/v) and producing lactic acid with a yield of at least 90% (w/w). Typically, the process includes a step of recovering lactic acid at a yield of at least 95% (v/v).

In one embodiment, the bioconversion competent *bacillus* strain is capable of growing on a test culture medium supplemented with 40% whey permeate (v/v) and producing lactic acid with a 90% yield (w/w). Typically, the process includes a step of recovering lactic acid at a yield of at least 95%.

In one embodiment, the bioconversion competent *Bacillus* strain is capable of growing on a test culture medium supplemented with 50% whey permeate (v/v) and producing lactic acid with a 90% yield (w/w). Typically, the process includes a step of recovering lactic acid at a yield of at least 95% (v/v).

In one embodiment, the bioconversion competent *Bacillus* strain is capable of converting DLP into lactic acid at a yield of at least 10 g lactic acid per litre of fermentation medium containing DLP. In one embodiment, the bioconversion competent *Bacillus* strain is capable of converting DLP into lactic acid at a yield of at least 30 g lactic acid per litre of fermentation medium containing DLP. In one embodiment, the bioconversion competent *Bacillus* strain is capable of converting DLP into lactic acid at a yield of at least 50 g lactic acid per litre of fermentation medium containing DLP. In one embodiment, the bioconversion competent *Bacillus* strain is capable of converting DLP into lactic acid at a yield of at least 60 g lactic acid per litre of fermentation medium containing DLP. In one embodiment, the bioconversion competent *Bacillus* strain is capable of converting DLP into lactic acid at a yield of at least 70 g lactic acid per litre fermentation medium containing DLP. In one embodiment, the bioconversion competent *Bacillus* strain is capable of converting DLP into lactic acid at a yield of at least 80 g lactic acid per litre fermentation medium containing DLP. In one embodiment, the bioconversion competent *Bacillus* strain is capable of converting DLP into lactic acid at a yield of at least 90 g lactic acid per litre of fermentation medium containing DLP. In one embodiment, the bioconversion competent *Bacillus* strain is capable of converting DLP into lactic acid at a yield of at least 100 g lactic acid per litre fermentation medium containing DLP.

In one embodiment, the culturing step is a fermentation step.

In one embodiment, the culturing step is a batch fermentation step.

In one embodiment, the culturing step is a fed batch fermentation step.

Various methods of separating lactic acid from fermentation broth are known in the art, including precipitation and filtration followed by ion exchange chromatography. In one embodiment, calcium is added to the fermentation broth to form an insoluble calcium lactate precipitate, which is filtered out of the broth and treated to release the lactic acid.

The culturing step is carried out during a culturing period during which lactose in the substrate is converted to lactic acid. In one embodiment, the culturing period is less than 100 hours. In one embodiment, the culturing period is less than 90 hours. In one embodiment, the culturing period is less than 80 hours. In one embodiment, the culturing period is less than 70 hours. In one embodiment, the culturing period is less than 60 hours. In one embodiment, the culturing period is less than 50 hours. In one embodiment, the culturing period is less than 40 hours. In one embodiment, the culturing period is less than 30 hours. In one embodiment, the culturing period is less than 20 hours. In one embodiment, the culturing period is less than 10 hours.

Typically, the process yield (i.e. yield of lactic acid) is at least 70% (w/w).

Typically, the process yield is at least 80% (w/w).
Typically, the process yield is at least 90% (w/w).
Typically, the process yield is at least 95% (w/w).

The invention also provides a method of converting a starting *Bacillus* strain into an adapted *Bacillus* strain having a greater tolerance to delactosed whey permeate than the starting strain, the method comprising the steps of:

culturing the starting strain of *Bacillus* in a first culture medium containing a first concentration of delactosed whey permeate (or concentrated whey permeate);

isolating a first colony of growing bacteria from the first culture medium;

culturing the first colony growing bacteria in a second culture medium containing a concentration of delactosed whey permeate (or concentrated whey permeate) that is higher than the first concentration; and isolating a second colony of growing bacteria from the second culture medium, in which the second colony of growing bacteria comprise an adapted *bacillus* strain.

In one embodiment, the colony of growing bacteria that are isolated have a colony morphology that matches the colony morphology obtained when the starting strain of *bacillus* is grown in a culture that is free of delactosed whey permeate (or free of concentrated whey permeate), for example tryptic soy agar. The colony morphology is typically a *Bacillus coagulans* morphology.

In one embodiment, the culturing step comprises growth on liquid media. In one embodiment, the isolation step comprises growth on solid media. Typically, for each round of culturing and isolation, the liquid media and solid media have the same concentration of delactosed whey permeate. In one embodiment, the culturing step comprises growth in liquid media and a sample of the liquid media is plated on solid media prior to isolation of colonies from the solid media plate. Typically, each round of culturing/isolation includes a step of sampling the liquid culture media after the culturing step for lactic acid concentration. This allows the identification of growing bacteria that are strong lactic acid producers.

In one embodiment, the process comprises at least three rounds of culturing/isolation steps. In one embodiment, the process comprises at least four rounds of culturing/isolation steps. In one embodiment, the process comprises at least five rounds of culturing/isolation steps. In one embodiment, the process comprises at least six rounds of culturing/isolation steps.

In one embodiment, the initial rounds of culturing/isolating comprise a first stepwise increase in DLP concentration, and the subsequent rounds of culturing/isolating comprise further stepwise increases in DLP, where the second stepwise increase in DLP concentration can be equal to or smaller than the previous stepwise increase in DLP concentration. Stepwise increase means that after each round of culturing/isolation, the concentration of DLP in the liquid media is increased in an iterative manner. In one embodiment, the first stepwise increase in DLP concentration is a stepwise increase of 8-12% DLP. In one embodiment, the first stepwise increase in DLP concentration is a stepwise increase of 9-11% DLP. In one embodiment, the first stepwise increase in DLP concentration is a stepwise increase of about 10% DLP. In one embodiment, the second stepwise increase in DLP concentration is a stepwise increase of 3-12% DLP. In one embodiment, the second stepwise increase in DLP concentration is a stepwise increase of 3-9% DLP. In one embodiment, the second stepwise increase in DLP concentration is a stepwise increase of about 5% DLP.

The invention also provides an adapted *Bacillus* strain (i.e. adapted *Bacillus coagulans* strain) produced according to a method of the invention.

In one embodiment, the starting *Bacillus coagulans* strain has a tolerance to DLP of less than 10% (v/v). Tolerance to DLP of X % means that the strain exhibits positive growth on solid media plates containing X % DLP as described below.

In one embodiment, the adapted *Bacillus* strain has a tolerance to DLP of at least 30%. In one embodiment, the adapted *Bacillus* strain has a tolerance to DLP of at least 40%. In one embodiment, the adapted *Bacillus* strain has a tolerance to DLP of at least 50%.

In one embodiment, the adapted *Bacillus* strain is capable of converting DLP into lactic acid at a yield of at least 10 g lactic acid per litre of DLP. In one embodiment, the adapted *Bacillus* strain is capable of converting DLP into lactic acid at a yield of at least 30 g lactic acid per litre of DLP. In one embodiment, the adapted *Bacillus* strain is capable of converting DLP into lactic acid at a yield of at least 50 g lactic acid per litre of DLP. In one embodiment, the adapted *Bacillus* strain is capable of converting DLP into lactic acid at a yield of at least 60 g lactic acid per litre of DLP. In one embodiment, the adapted *Bacillus* strain is capable of converting DLP into lactic acid at a yield of at least 70 g lactic acid per litre of DLP. In one embodiment, the adapted *Bacillus* strain is capable of converting DLP into lactic acid at a yield of at least 80 g lactic acid per litre of DLP. In one embodiment, the adapted *Bacillus* strain is capable of converting DLP into lactic acid at a yield of at least 90 g lactic acid per litre of DLP. In one embodiment, the adapted *Bacillus* strain is capable of converting DLP into lactic acid at a yield of at least 100 g lactic acid per litre of DLP.

In one embodiment, the starting *bacillus* strain is a *Bacillus coagulans*.

In one embodiment, the adapted *Bacillus* strain is selected from UCD1 and UCD2, or derivatives thereof adapted to grow in higher concentrations of DLP, or convert DLP to lactic acid with greater yield or efficiency. The process of adaption of the invention may be employed to generate derivatives of UCD1 or UCD2, or MG-2.

The invention also relates to a derivative of MG-2 characterised in that it is adapted to grow in higher concentrations of DLP, or convert DLP to lactic acid with greater yield or efficiency, compared with ML-2.

The invention also relates to an adapted strain of the invention in a freeze-dried or frozen format.

Definitions

"Lactic acid" is an organic compound with the formula $CH_3CHCO_2H$. It is a chiral compound existing in two forms, known as optical isomers, namely D-lactic and L-lactic acid. In the current embodiment, the lactic acid produced with the process and adapted bacteria of the invention is predominantly L-lactic acid (for example >98% v/v). In one embodiment, the term "lactic acid" as used herein should be understood to mean L-lactic acid.

"Whey permeate": Whey is the liquid remaining after milk has been curdled and strained. It is a by-product of the manufacture of cheese and casein. It can exist as sweet whey or acid whey. The whey may be obtained from bovine milk or milk from other mammals such as goats or sheep. Preferably, the milk is bovine milk. Whey permeate is produced by removing protein and other solid components from whey. It is generally produced by treating liquid whey to ultrafiltration or diafiltration. Whey permeate typically contains at least 40 g lactose per litre. Typically, whey permeate contains 1900 to 7600 ppm chloride. The term "whey permeate" also includes concentrated whey permeate (CWP), a product derived from whey permeate evaporation. Typically, concentrated whey permeate contains 200-240 g lactose per litre. An exemplary composition of CWP is provided in Table 3 below. Typically, CWP contains contains at least 5,000, 6,000, 7,000, 8,000, 10,000, 15,000, or 20,000 ppm chloride. In one embodiment, the DLP contains 5,000 to 22,000 ppm chloride.

"Delactosed whey permeate" or "DLP" is a by-product of processing of whey permeate to remove lactose that contains at least 200 g lactose per litre of DLP. Lactose removal from whey is quite inefficient, and typically about 50% lactose is removed. After lactose removal by crystallisation, the liquor is concentrated, which means that the DLP has a higher amount of lactose post filtration compared with whey permeate, and higher amounts of salts and minerals, especially chlorides and phosphates. Thus, the term "delactosed" is somewhat of an anomaly. Typically DLP contains at least 200 g or in one embodiment at least 240 g lactose per litre. Typically, DLP contains at least 10,000, 15,000, 20,000, 30,000, 40,000, 50,000, or 60,000 ppm chloride. In one embodiment, the DLP contains 15,000 to 62,000 ppm chloride. In one embodiment, the DLP contains 240-400 g lactose per litre of DLP. An exemplary composition of delactosed whey permeate is provided in Table 1 below.

"Culture medium" (or growth medium) is a liquid or solid preparation designed to support the growth of bacteria. Examples include nutrient broths and agar plates. Examples of solid and liquid culture media are described below. A culture medium containing at least 10% DLP (v/v) means that 10% of the culture medium by volume is made up of DLP.

"Bioconversion-competent strain of *bacillus*" means a strain of *Bacillus* bacteria (in particular a strain of *Bacillus coagulans*) that is capable of growing on a test culture medium containing at least 10% delactosed whey permeate (v/v) typically having at least 240 g lactose per litre DLP and converting DLP into lactic acid at a yield of at least 50%. In one embodiment, the bioconversion competent *Bacillus* strain is adapted to grow in delactosed whey permeate. Methods for detecting positive growth, and lactic acid production, of *Bacillus* strains on DLP containing media are described below. In one embodiment, a test *bacillus* strain is inoculated in liquid medium containing 10% (v/v) DLP and incubated at 54'C for 24 h. Growth can be determined using standard test to detect bacterial growth in culture, including measuring changes in optical density using a spectrophotometer at 600 nm before and after incubation, or by means of a plate count assay. Lactic acid production in the culture medium can be determined using standard methods in the art, for example HPLC.

"Test culture medium" means the solid media described below (Solid Media Preparation).

"*Bacillus coagulans*" is a lactic acid forming bacterial species within the genus *Bacillus*. It is a gram positive rod, and generally catalase forming, spore forming, motile and a facultative anaerobe. An example of a *Bacillus coagulans* is a strain of *Bacillus coagulans* MG-2 isolated from soil and identified by 16S rDNA sequencing. Other examples of *Bacillus coagulans* are described in the literature and available from Depository Institutions such as the NCIMB in Scotland (http://www_ncimb_com/) and DSMZ in Germany (https://www_dsmz_de/).

"Wild-type *bacillus* strain" means a strain of *bacillus* bacteria that exists in nature e.g. *B. coagulans* MG-2 isolated from soil (described below).

"Adapted to grow in delactosed whey permeate" means that the adapted strain is produced in an iterative or stepwise culturing process in which the concentration of DLP in the culture medium is increased in each step of the process thereby producing an adapted derivative strain of *Bacillus* that is capable of growing in a higher concentration of DLP that the non-adapted (starting) strain. The term "tolerance" as applied to the adapted strain means that the strain is adapted to be more tolerant to growth on DLP. An example is a strain of *Bacillus coagulans* that is unable to grow on solid media containing 10% DLP, but that as a result of the adaption process of the invention is adapted such that it can grow on such media. Bacterial adaption can change the genotype and phenotype of bacteria. The term "growing bacteria" means bacteria that are capable of replicating.

"Adapted *Bacillus* strain" means a strain of *Bacillus*, typically a strain of *Bacillus coagulans*, that has been adapted in an adaption process to be more tolerant to DLP (i.e. can grow, or can grow better) than the non-adapted (starting) strain. In one embodiment, the adapted *Bacillus* strain has been adapted according to a method of the invention. In one embodiment, the starting *Bacillus* strain is not bioconversion competent, but the adapted strain is bioconversion competent. Examples of adapted strains are described below (UCD1 and UCD2). The starting *Bacillus* strain can be isolated from nature or obtained from a culture deposit. An example of a starting strain is MG-2 strain described below. Examples of deposited strains of *Bacillus coagulans* include strains J112 (PTA-13253), WCP 10-4 (PTA-13255), ATCC 7050, ATCC 31284, NCTC 10334.

"Batch fermentation" means a process in which bacteria convert a substrate into a product in a fermenter. It is typically a closed system in which all the nutrients and other additives are added to the system at the start of the process. "Fed batch fermentation" is a similar process in which additives (for example additional nutrients) are added to the fermenter during the process.

"Colony of growing bacteria" refers to a colony of *Bacillus* bacteria grown in a solidified medium containing DLP and which exhibit "positive growth", meaning exhibiting a colony morphology that matches (i.e. similar size and shape) the colony morphology of the same bacteria when grown in a culture medium that is free of DLP, for example Tryptic Soy Agar (TSA). The latter colony morphology may be a typical colony morphology for *Bacillus coagulans*, which would be known to the skilled person and availably from Bergeys Manual of Archaea and Bacteria (Online ISBN: 9781118960608).

"Round of culturing/isolation" means a step of culturing bacteria (typically in a liquid medium) and then isolating bacteria (typically in a solid medium).

"Stepwise increase in DLP concentration" in the context of a process for producing an adapted *Bacillus* strain that involves several rounds of culturing/isolating means that the concentration of DLP in the culture medium is increased after each round of culturing/isolating.

"Tolerance to DLP of X %" means that the strain exhibits positive growth when grown in a test culture medium containing 10% DLP (v/v).

"Yield" in the context of production of lactic acid means the % (w/w) of the lactose in the substrate that is converted into lactic acid. Thus, if the substrate in the fermentation broth (i.e. concentrated whey permeate or DLP) initially contains 200 g of lactose and the process produces 100 g of lactic acid and, this is a yield of 50% (w/w).

"Yield" in the context of recovery of lactic acid means the % (w/w) of lactic acid produced that is recovered in a recovery step. Thus, if 20 litres of lactic acid are produced in a fermentation broth, and 18 litres are recovered from the broth, this is a yield 90% (v/v). Method of determining % yield may be determined using HPLC where lactose and lactic acid can be detected by refractive index

DETAILED DESCRIPTION OF THE INVENTION

Experimental:
Solid Media Preparation

The following solid components were mixed in water until completely dissolved and autoclaved at 121° C. for 15 min. (the amounts of solid additions were calculated to give the amounts below after the addition of DLP to the media)

| Yeast extract | 10 g/l |
|---|---|
| Bis-tris | 10 g/l |
| Agar | 1.5 g/l |
| $NH_4H_2PO_4$ | 2 g/l |
| $(NH_4)_2SO_4$ | 3.5 g/l |

The DLP was autoclaved at 105° C. for 15 min. This temperature was chosen to minimize the amount of lactose loss due to heat and pH dependent Maillard reaction which would be higher at the normal autoclave conditions (121° C. for 15 mins) used to sterilize microbiological media. It was then mixed with the other sterile media components at the desired concentration.

| DLP | 10-50% (v/v) |
|---|---|

The media was adjusted to pH 6.5 with 6 M NaOH and poured into petri dishes and then allowed to solidify.
Liquid Media Preparation The following solid components were mixed in water until completely dissolved (the amounts of solid additions were calculated to give the amounts below after the addition of DLP to the media)

| Yeast extract | 10 g/l |
|---|---|
| Bis-tris | 10 g/l |
| $NH_4H_2PO_4$ | 2 g/l |
| $(NH_4)_2SO_4$ | 3.5 g/l |

The DLP was autoclaved at 105° C. for 15 min to minimize the amount of lactose loss due to heat and pH dependent Maillard reaction. It was then mixed with the other sterile media components at the desired concentration.

| DLP | 10-50% (v/v) |
|---|---|

The media was adjusted to pH 6.5 with 6 M NaOH
Adaptation Process

*B. coagulans* cannot grow on whey permeate 20% or DLP above 10% volume per volume of growth medium (v/v)

1. The WT *Bacillus Coagulans* was inoculated on to solid media plates with a range of DLP concentrations (5, 10, 15, 20, 25, 30 and 35% v/v) to determine the growth threshold of the starting strain (wild type (WT)) on DLP.
2. Plates were incubated at 54° C. for 16 h, positive growth was determined as colonies matching the time taken to appear on the solid growth media as that of the WT strain when grown on TSA plates containing 5% DLP under the same incubation conditions.

3. Colonies were determined to be tolerant of 10% (v/v) DLP. Some small colonies were observed at 15% but they did not match the criteria for positive growth outlined in point 2. No colonies were observed at concentrations of 20% and above DLP.
4. Colonies from plates containing 10% DLP were transferred to liquid media containing 15% DLP, these cultures were incubated without shaking in test tubes at 54° C. for 96 hours.
5. Samples were taken from these cultures every 24 h and plated on to solid media containing 15% DLP and incubated as described in point 2. Many colonies were observed from time point 48 to 96 h, but only colonies that met the criteria for positive growth outlined in point two were taken forward for further adaptation by repeating the procedure with the colonies capable of growth at 15% DLP used as the inoculum for liquid culture with 20% DLP.
6. This process was repeated using 20 to 40% DLP over a number of months. At this point the 5% incremental increases that had been successful in adapting the strain from 10% DLP to 40% DLP tolerance ceased to deliver the same rate of adaptation. The colonies matching the criteria for positive growth at 40% were stocked and designated as *Bacillus Coagulans* UCD 1
7. To adapt the strain to higher concentrations of DLP 2% increments were employed with the same sampling and screening methods as described above. These were repeated until colonies matching the criteria for positive growth were isolated on plates containing 50% DLP on solid media. These colonies were stocked and designated *Bacillus Coagulans* UCD2.
8. Both UCD 1 and UCD 2 were screened for the ability to produce LA from WP and DLP, these adapted strains were capable of LA production using WP (50% v/v) and DLP (50% (v/v)) as the sole source of lactose. The Wild type strain did not grow on WP or DLP at 50% (v/v).

Isolation of MG-2

Soil samples from UCD were inoculated in liquid medium containing 30% (v/v) DLP and incubated at 54'C for 24 h. Next, media were inoculated onto solid media and incubated for 24 h at 54'C. Isolates were collected and verified for lactic acid production using HPLC. A sample of media is filtered to remove bacterial cells, the sample is then run on a BioRad HPX-87H hplc column with a flow rate of 0.55 ml min of 0.0014 M H2SO4 as the mobile phase. Standard curves of lactic acid and lactose are prepared using analytical standards from sigma aldrich and run in the same manner. Peak area from the media samples for LA and lactose are compared to the standard curve and the yield is determined by comparing the amount of lactose utilised to the amount of lactic acid produced.

One isolate MG-2 was identified as *Bacillus coagulans*. It produced LA when grown on WP and DLP.

The invention is not limited to the embodiments hereinbefore described which may be varied in construction and detail without departing from the spirit of the invention.

TABLE 1

Typical Composition of DLP

| | Calcium (ppm) | Phosphate (ppm) | Chloride (ppm) | Sodium (ppm) | Potassium (ppm) | Magnesium (ppm) | Sulphate (ppm) | Dry Matter (DM) % | Ash % of DM | Protein % DM | Fat % (DM) | Lactose and other organics % (DM) |
|---|---|---|---|---|---|---|---|---|---|---|---|---|
| Min | 827.5 | 4075 | 15450 | 6447.5 | 14580 | 735 | 3405 | 24 | 20 | 5 | 0.1 | 60 |
| Average | 1655 | 8150 | 30900 | 12895 | 29160 | 1470 | 6810 | 33 | 24 | 8 | 0.7 | 68 |
| Max | 3310 | 16300 | 61800 | 25790 | 58320 | 2940 | 13620 | 40 | 28 | 10 | 2 | 75 |

DM = dry matter,
PPM = part per million,
% w/v = percentage weight per volume

TABLE 2

Typical composition of Whey permeate (WP)

| | Calcium (ppm) | Phosphate (ppm) | Chloride (ppm) | Sodium (ppm) | Potassium (ppm) | Magnesium (ppm) | Sulphate (ppm) | Dry Matter (DM) % | Ash % of DM | Protein % DM | Fat % (DM) | Lactose and other organics % (DM) |
|---|---|---|---|---|---|---|---|---|---|---|---|---|
| Min | 175 | 480 | 1900 | 569 | 1348 | 65 | 668 | 6 | 0.75 | 2 | 0.1 | 80 |
| Average | 349 | 960 | 3800 | 1137 | 2696 | 129 | 1337 | 10 | 1.5 | 4 | 0.4 | 86 |
| Max | 699 | 1920 | 7600 | 2274 | 5392 | 259 | 2673 | 12 | 3 | 6 | 1 | 90 |

DM = dry matter,
PPM = part per million,
% w/v = percentage weight per volume

TABLE 3

Typical composition of concentrated WP (CWP)

| | Calcium (ppm) | Phosphate (ppm) | Chloride (ppm) | Sodium (ppm) | Potassium (ppm) | Magnesium (ppm) | Sulphate (ppm) | Dry Matter (DM) % (w/v) | Ash % of DM | Protein % DM | Fat % (DM) | Lactose and other organics % (DM) |
|---|---|---|---|---|---|---|---|---|---|---|---|---|
| Min | 524 | 1440 | 5700 | 1705.5 | 4044 | 194 | 2005 | 18 | 0.75 | 2 | 0.1 | 80 |
| Average | 1048 | 2880 | 11400 | 3411 | 8088 | 388 | 4010 | 30 | 1.5 | 4 | 0.4 | 85.6 |
| Max | 2096 | 5760 | 22800 | 6822 | 16176 | 776 | 8020 | 36 | 3 | 6 | 1 | 90 |

DM = dry matter,
PPM = part per million,
% w/v = percentage weight per volume

TABLE 4

Strain Tolerance of concentrated WP and DLP

| Strain | CWP Tolerance (%) | DLP Tolerance (%) | Lactic Acid Yield % cWP | Lactic Acid Yield % DLP |
|---|---|---|---|---|
| B. Coagulans Wild Type | 20 | 10 | 50 | 50 |
| B. Coagulans UCD 1 | 60 | 40 | 90 | 90 |
| B. Coagulans UCD 2 | 70 | 50 | 90 | 90 |
| B. Coagulans MG2 | 70 | 50 | 90 | 90 |

The invention claimed is:

1. A method for producing lactic acid comprising steps of: culturing in a fermentation broth comprising culture medium and delactosed or concentrated whey permeate as a substrate a bioconversion competent *Bacillus coagulans* bacterial strain capable of bioconversion of delactosed whey permeate in the fermentation broth into lactic acid and in which the fermentation broth comprises 10-50% (v/v) delactosed or concentrated whey permeate; and recovering the lactic acid from the culture medium wherein the delactosed whey permeate substrate comprises at least 60% lactose and other organics (% dry matter) and at least 15,000 ppm chloride, and the concentrated whey permeate substrate comprises at least 80% lactose and other organics (% dry matter) and at least 5,000 ppm chloride, in which the bioconversion competent *Bacillus coagulans* strain is an adapted *Bacillus coagulans* strain that is adapted to grow in a test culture medium containing at least 30% delactosed whey permeate (v/v), wherein the yield of lactic acid is at least 70% (w/w).

2. A method according to claim 1 in which the bioconversion competent *Bacillus coagulans* strain is capable of converting delactosed whey permeate into lactic acid at a yield of at least 90% (w/w) and in which lactic acid is recovered from the fermentation broth at a yield of at least 95% (v/v).

3. A method according to claim 1, in which the *Bacillus coagulans* strain is an adapted *Bacillus coagulans* strain that is obtained by a method comprising the steps of:

culturing a starting strain of *Bacillus coagulans* in a first culture medium containing a first concentration of delactosed whey permeate;
isolating a first colony of growing bacteria from the first culture medium;
culturing the growing bacteria in a second culture medium containing a concentration of delactosed whey permeate that is higher than the first concentration; and
isolating a second colony of growing bacteria from the second culture medium, in which the second colony of growing bacteria comprise an adapted *Bacillus* strain.

4. A method according to claim 3 including at least three rounds of culturing plus isolation steps.

5. A method according to claim 3 including a step of assaying the culture medium after each culturing step for lactic acid.

6. A method according to claim 1 in which the lactic acid product comprises at least 90% L-lactic acid by volume.

7. A method according to claim 1, in which the substrate is delactosed whey permeate comprising at least 200 g lactose per litre and at least 15,000 ppm chloride.

8. A method according to claim 1, in which the bioconversion competent *Bacillus coagulans* strain is capable of converting delactosed whey permeate into lactic acid at a concentration of at least 80 g lactic acid per litre of culture medium.

9. A method according to claim 1, in which the bioconversion competent *Bacillus coagulans* strain is capable of converting delactosed whey permeate into lactic acid at a concentration of at least 100 g lactic acid per litre of culture medium.

10. A method according to claim 1, in which the fermentation broth comprises 10-50% (v/v) delactosed whey permeate.

11. A method according to claim 1, in which the yield of lactic acid is at least 80% (w/w).

12. A method according to claim 1, in which the yield of lactic acid is at least 90% (w/w).

13. A method according to claim 1, in which the yield of lactic acid is at least 95% (w/w).

* * * * *

UNITED STATES PATENT AND TRADEMARK OFFICE
CERTIFICATE OF CORRECTION

Page 1 of 1

PATENT NO.        : 10,927,390 B2
APPLICATION NO.   : 15/772046
DATED             : February 23, 2021
INVENTOR(S)       : Kevin O'Connor et al.

It is certified that error appears in the above-identified patent and that said Letters Patent is hereby corrected as shown below:

On the Title Page

Item (73) Assignee, delete "GLANBIA IRELAND DESIGNATED ACTIVITY COMPANY, Ballyraggat (IE)" and insert -- GLANBIA IRELAND DESIGNATED ACTIVITY COMPANY, Ballyraggat, Co. Kilkenny (IE) --.

Signed and Sealed this
Eighteenth Day of May, 2021

Drew Hirshfeld
*Performing the Functions and Duties of the*
*Under Secretary of Commerce for Intellectual Property and*
*Director of the United States Patent and Trademark Office*